(12) United States Patent
Coffeng

(10) Patent No.: US 9,101,335 B2
(45) Date of Patent: Aug. 11, 2015

(54) METHOD, ARRANGEMENT AND COMPUTER PROGRAM PRODUCT FOR MANAGING ALARMS IN PATIENT MONITORING

(75) Inventor: Rene Coffeng, Helsinki (FI)

(73) Assignee: General Electric Company, Schenectady, NY (US)

( * ) Notice: Subject to any disclaimer, the term of this patent is extended or adjusted under 35 U.S.C. 154(b) by 243 days.

(21) Appl. No.: 13/163,970

(22) Filed: Jun. 20, 2011

(65) Prior Publication Data

US 2012/0319848 A1 Dec. 20, 2012

(51) Int. Cl.
*G08B 1/08* (2006.01)
*A61B 5/00* (2006.01)
*A61M 16/00* (2006.01)

(52) U.S. Cl.
CPC ............ *A61B 5/746* (2013.01); *A61M 16/0051* (2013.01); *A61M 2205/505* (2013.01); *A61M 2205/584* (2013.01); *A61M 2230/42* (2013.01); *A61M 2230/432* (2013.01)

(58) Field of Classification Search
CPC ... A61B 5/0002; A61B 5/0006; A61B 5/7275
USPC .......................................... 340/573.1, 539.12
See application file for complete search history.

(56) References Cited

U.S. PATENT DOCUMENTS

| | | | | |
|---|---|---|---|---|
| 5,069,668 A * | 12/1991 | Boydman | ...................... | 604/121 |
| 5,262,944 A * | 11/1993 | Weisner et al. | ................ | 600/300 |
| 5,417,222 A * | 5/1995 | Dempsey et al. | ............ | 600/509 |
| 7,629,890 B2 * | 12/2009 | Sullivan et al. | ............ | 340/573.1 |
| 8,165,893 B1 * | 4/2012 | Goldberg et al. | ................. | 705/2 |
| 2002/0190863 A1 * | 12/2002 | Lynn | ........................... | 340/573.1 |
| 2004/0214148 A1 * | 10/2004 | Salvino et al. | ................. | 434/262 |
| 2004/0249249 A1 * | 12/2004 | Lawson et al. | ................. | 600/300 |
| 2005/0177096 A1 * | 8/2005 | Bollish et al. | ..................... | 604/65 |
| 2006/0047538 A1 * | 3/2006 | Condurso et al. | ................. | 705/3 |
| 2007/0255250 A1 * | 11/2007 | Moberg et al. | ................ | 604/503 |
| 2008/0281168 A1 * | 11/2008 | Gibson et al. | ................. | 600/301 |
| 2008/0300572 A1 * | 12/2008 | Rankers et al. | ............... | 604/504 |
| 2009/0069642 A1 * | 3/2009 | Gao et al. | ....................... | 600/300 |
| 2009/0164251 A1 * | 6/2009 | Hayter | ............... | 705/3 |
| 2009/0275805 A1 * | 11/2009 | Lane et al. | ..................... | 600/300 |
| 2010/0268304 A1 * | 10/2010 | Matos | ............................. | 607/60 |
| 2010/0285082 A1 * | 11/2010 | Fernandez | .................... | 424/422 |
| 2011/0077574 A1 * | 3/2011 | Sigg et al. | ..................... | 604/6.01 |
| 2011/0082440 A1 * | 4/2011 | Kimmo et al. | ............... | 604/503 |

OTHER PUBLICATIONS

Tautz et al., "Case Scenario: Increased End-tidal Carbon Dioxide: A Diagnostic Dilemma", Anesthesiology, vol. 112, No. 2, Feb. 2010.
Atlee, "Complications in anesthesia", Elsevier Health Sciences, p. 878, 2007.

* cited by examiner

*Primary Examiner* — Jennifer Mehmood
*Assistant Examiner* — Emily C Terrell
(74) *Attorney, Agent, or Firm* — Andrus Intellectual Property Law, LLP

(57) ABSTRACT

A method, device, and computer program product for managing alarms during a care process are disclosed. Care is provided to a subject according to settings of at least one care device and physiological parameters obtained from the subject are monitored, wherein the monitoring comprises triggering an alarm in response to detection of an alarm event. To enable smooth transfer from an alarm event to normal monitoring state, at least one available control option is determined for recovering from the alarm event. A user is prompted to select one of the at least one available control option, thereby to obtain a user-selected control option and the settings of the at least one care device are adjusted according to the user-selected control option.

12 Claims, 4 Drawing Sheets

METHOD, ARRANGEMENT AND COMPUTER PROGRAM PRODUCT FOR MANAGING ALARMS IN PATIENT MONITORING

BACKGROUND OF THE INVENTION

This disclosure relates generally to patient monitoring. More particularly, the present invention relates to management of alarms triggered during patient monitoring.

Patient monitors are electronic devices designed to display physiological information about a subject. Electrocardiogram (ECG), electroencephalogram (EEG), plethysmographic signals, and signals related to blood pressure, temperature, and respiration represent typical physiological information contained in full-size patient monitors. Patient monitors are typically also furnished with alarming functionality to alert the nursing staff when a vital sign or physiological parameter of a patient exceeds or drops below a preset limit. Alarms are normally both audible and visual effects aiming to alert the staff to a life-threatening condition or to another event considered vital. In most monitors, the alarm limits may be defined by the user, since the limits typically depend on patient etiology, age, gender, medication, and various other subjective factors. Each specific physiological parameter, such as heart rate or blood pressure, may also be assigned more than one alarm limit.

In addition to individual sensor/parameter alarms, patient monitors can be configured to raise combinatory alarms. That is, several physiological parameters may be used to determine a combined index and to give an alarm when the combined index fulfills a specific criterion. The combinatory alarms may range from simple combinations like "low heart rate and low arterial pressure" to complex rule-based scenarios used in various clinical expert systems. These systems help the medical staff to use standardized guidelines and treatment procedures and support the medical staff in clinical decision-making. However, due to the complexity of the built-in intelligence of such systems, it may be difficult for a clinician to grasp the connection between an alarm and the underlying physiological behavior of the patient.

Since it is difficult for a caregiver to control a plurality of stand-alone devices and to interpret the information obtained from a plurality of devices, present patient monitoring devices are often integrated devices in which many capabilities are integrated and in which the built-in intelligence helps the caregiver to get an overall picture of the true status of the patient. For example, monitoring devices used in operating theatres are often provided with ventilation and drug delivery facilities, so that a single monitoring device may offer integration through the entire treatment period.

Due to the integration, these devices are provided with an increasing amount of user-adjustable control parameters, such as ventilation and drug therapy control parameters, to adapt the care processes to the current status of the patient concerned. The care processes are during the course of treatment continuously optimized to give the patient as safe and high quality therapy as possible.

However, the devices are not fully automated closed loop control devices, but user action is needed in response to an alarm event. The problem related to the alarm events is the adaptation of the care processes to the current situation. When an alarm is triggered, the user(s) do not normally know straight away, what would be the optimal way of recovering from the alarm situation to get the patient and the monitoring process back to normal alarm-free state. Therefore, users tend to control the care processes through trial and error. The particular user setting that needs to be controlled to achieve a certain output is not always clearly identifiable. That is, the new values that a user sets for the control parameters in response to an alarm tend to cause overshoot and/or undershoot and therefore also new alarms. The relations between input control parameters and output variables are sometimes simple linear first order relations. However, a change in the operation point may cause non-proportional effects. For example, a change in the end expiratory pressure of lung ventilation may cause non-proportional effects to the respiration due to recruitment of lung alveoli. More complex non-linear physiological systems with difficulties with time constant estimation involve gas exchange and drug concentration changes, which may lead to neurological and hemodynamic changes. Due to the above reasons, the users are not always able to adapt the care processes smoothly to the current situation and the present-day open-loop patient monitors are not able to assist the users in this task to ensure smooth transfer from an alarm event to normal state.

BRIEF DESCRIPTION OF THE INVENTION

The above-mentioned problems are addressed herein which will be comprehended from the following specification. In the alarm management mechanism disclosed, normal and easily comprehensible alarm events are maintained and the user is assisted by determining the best control options available for recovering from the alarm. The options are presented to the user in response to an alarm event so that the user may promptly initiate control of the care processes to return the monitoring process to normal, i.e. alarm-free, state.

In an embodiment, a method for managing alarms during a care process comprises providing care to a subject according to settings of at least one care device and monitoring physiological parameters obtained from the subject, wherein the monitoring comprises triggering an alarm in response to detection of an alarm event. The method further comprises determining at least one available control option for recovering from the alarm event, prompting a user to select one of the at least one available control option, thereby to obtain a user-selected control option, and adjusting the settings of the at least one care device according to the user-selected control option.

In another embodiment, an arrangement for managing alarms during a care process comprises at least one care device adapted to provide care to a subject and a monitoring unit adapted to monitor physiological parameters obtained from the subject, wherein the monitoring unit is further adapted to trigger an alarm in response to detection of an alarm event. The arrangement further comprises a determination unit adapted to determine at least one available control option for recovering from the alarm event, a user interface unit configured to prompt a user to select one of the at least one available control option, thereby to obtain a user-selected control option, and an adjustment unit adapted to adjust settings of the at least one care device according to the user-selected control option.

In a still further embodiment, a computer program product for managing alarms during a care process comprises a first program product portion adapted to determine at least one available control option for recovering from an alarm event, a second program product portion adapted to prompt a user to select one of the at least one available control option, thereby to obtain a user-selected control option, and a third program product portion adapted to adjust settings of the at least one care device according to the user-selected control option.

Various other features, objects, and advantages of the invention will be made apparent to those skilled in the art from the following detailed description and accompanying drawings.

DETAILED DESCRIPTION OF THE INVENTION

Figure 1:
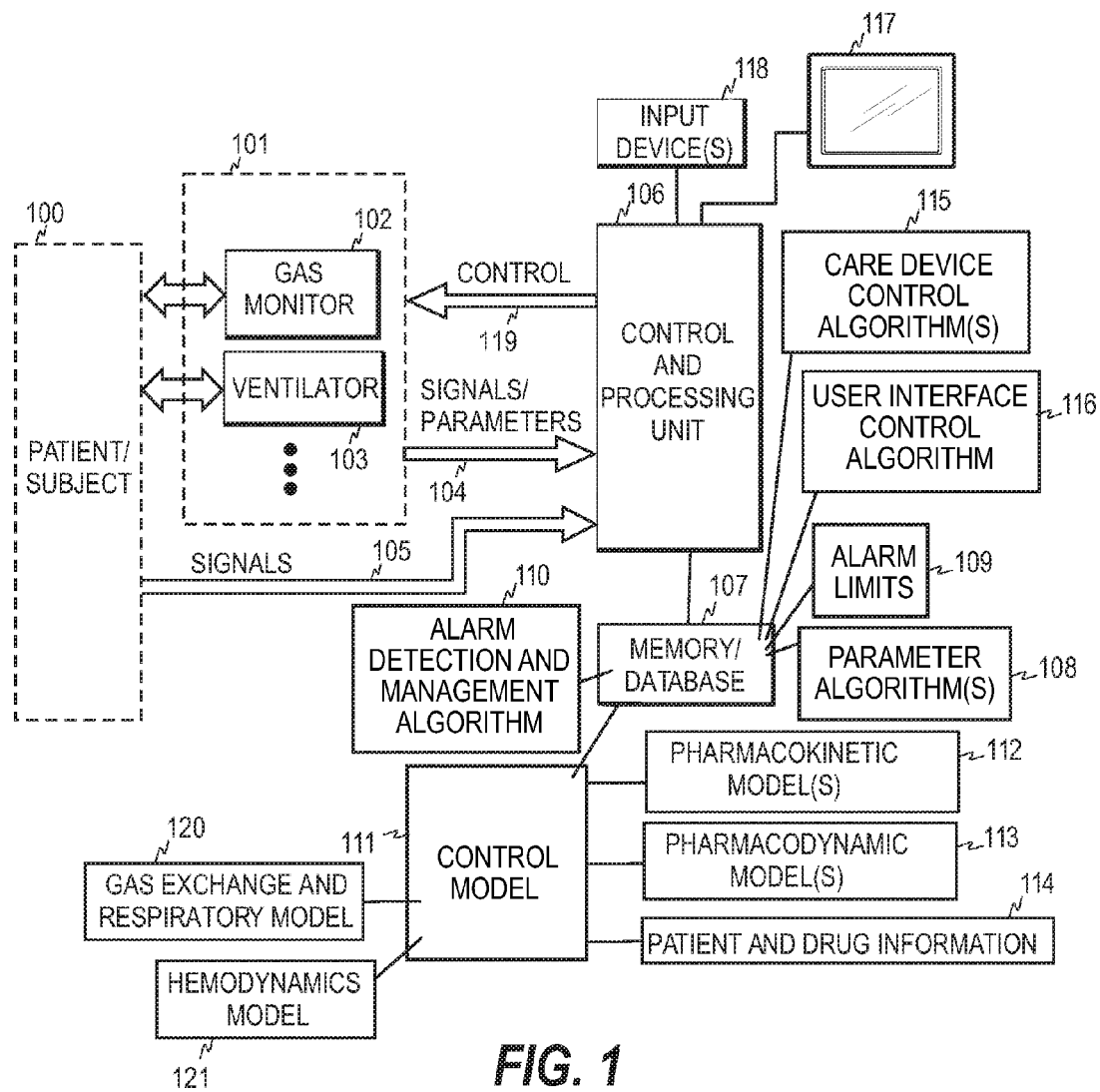
FIG. 1 illustrates one embodiment of an apparatus or system for providing care to a subject.

FIG. 1 illustrates one embodiment of a monitoring apparatus/system for monitoring a subject 100. The care process involves that care is provided to the subject through a care unit 101 comprising one or more care devices, such as a gas monitor 102 and a ventilator 103. The combination of a gas monitor and a ventilator is common in operating theatres, for example. The monitoring apparatus/system normally acquires a plurality of physiological signals from the subject and derives physiological parameters based on the physiological signals. The physiological parameters may in this example be determined in a control and processing unit 106 of the apparatus/system based on physiological signals obtained from the care devices or from the subject, cf. arrows 104 and 105. The physiological signals may be supplied to the control and processing unit 106 through a pre-processing stage (not shown) comprising typically an input amplifier and a filter, for example. The physiological parameters may also be determined in the care unit 101, in which case the control and processing unit receives a time series of each parameter from the care unit, cf. arrow 104.

In a normal monitoring situation, care is given to the subject according to the current settings of the care device(s) and the physiological parameters are monitored by the apparatus/system. When the apparatus/system detects an alarm event, such as a crossing of an alarm limit, an alarm is triggered and indicated to the user. As the disclosed monitoring mechanism concerns alarm management, the apparatus/system is discussed in terms of the alarm management in the following.

For the determination of the physiological parameters, the control and processing unit 106 may be provided with one or more parameter algorithms 108 which may be stored in a memory 107 to be executed by the control and processing unit, thereby to obtain the time series of the physiological parameters to be monitored. The memory may further store a plurality of alarm limits 109, each limit forming an alarm limit for a particular parameter. For the management of alarms, the control and processing unit may further be provided with an alarm detection and management algorithm 110 adapted to detect alarm events and manage alarms. The algorithm may be provided with a control model 111 adapted to model recovery strategies from an alarm event to normal monitoring state, i.e. the model is configured to evaluate how well different control scenarios are able to restore the subject from an alarm situation to normal state. After an alarm event, algorithm 110 may use the control model to find the best available recovery options. The control model may include a pharmacokinetic model 112 and/or a pharmacodynamic model 113 for evaluating drug effects. Generally, a pharmacokinetic model describes how the drug is distributed in the course of time from the site of delivery to different parts of the body and to the particular organ, such as the brain, in which the drug is supposed to have its effect. A pharmacokinetic model comprises of a set of mathematical differential equations that describes the distribution of a drug within the body as a function of time. The model includes both drug-specific and patient-specific parameters and therefore also patient and drug information 114 is stored in the memory/model. The drug-specific parameters describe the diffusion and solubility properties of the drug, whereas the patient-specific parameters describe the properties of the patient that affect the drug distribution, such as weight, height, age, and gender. The body of the patient is represented by a simplified system of typically three tissue compartments among which the drug is distributed according to the differential equations. A pharmacodynamic model 113 in turn defines the effect of the drug as a function of its concentration at the site at which it is effective, i.e. effect-site concentration. Such models may also use anthropometric data. For hypnotic drugs the effect is the hypnotic state of the patient, whereas the effect-site is the brain. The control model may also include a gas exchange and respiratory model 120 configured to predict responses to changes in ventilator settings. Further, the control model may include a hemodynamics model 121 configured to predict cardiorespiratory interactions resulting from changes in ventilator settings.

For controlling the care device(s), the control and processing unit may use one more care device control algorithms 115. As discussed below, the controlling of the care devices in connection with an alarm event occurs after user interaction, since the final decision on the particular control operation to be applied in response to an alarm event is made by the user.

To interact with the user, the control and processing unit may employ a user interface control algorithm 116 adapted to control a display unit 117 for displaying various information to the user and to receive user input information. The user may supply information to the apparatus/system through one or more user interface devices 118, such as a keyboard and/or a mouse.

The control model 111 of the apparatus/system may also be stored in a memory/database of a network, such as hospital LAN or the Internet. In these embodiments, the network element provided with the control model searches for the best available control option(s) in response to the requests received from the monitoring devices and returns the list of available options to the requesting device.

The priority of the available control options may be based on a database providing one or more reactions in order of prevalence in previous similar cases derived from an expert system database. The history of recent changes in the settings of this particular patient may also be weighted into the priority order. In addition, logical operations or fuzzy logic models, as to which of the possible settings to change, may be based on limits of the normal ranges in which the input settings can vary. The effect of an input change on possible output variables may be evaluated using a prediction model, and if a certain setting causes some secondary parameters to get close to alarm limits, the priority of that option will be decreased. The magnitude of the advised change in the settings may be based on a prediction model to make the output parameter return to normal value range.

Figure 2:
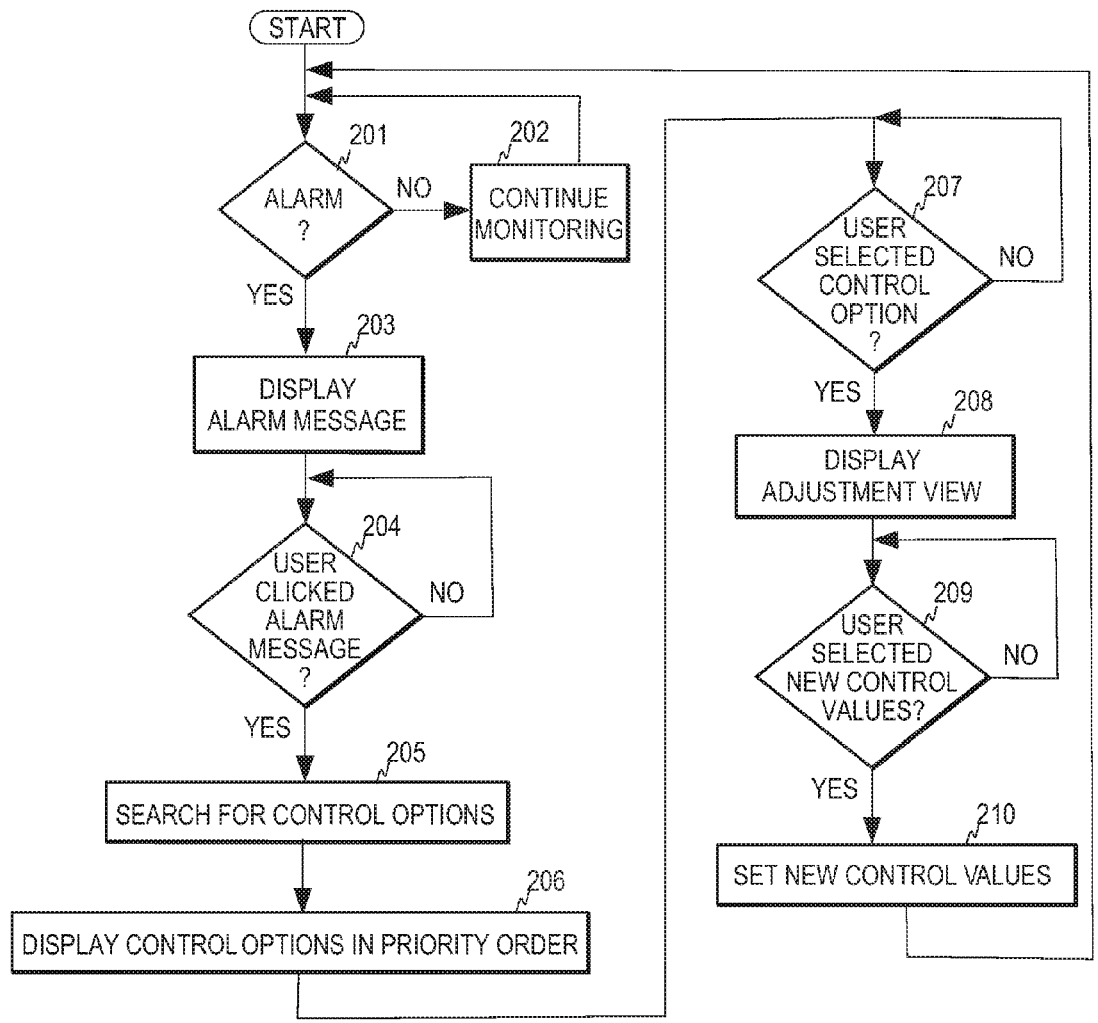
FIG. 2 is a flow diagram illustrating one embodiment of the alarm management carried out in the apparatus/system of FIG. 1.

FIG. 2 is a flow diagram illustrating an example of the operation of the alarm detection and management and user interface control algorithms 110 and 116. During the monitoring of the subject 100, the control and processing unit 106 continuously monitors for alarm events (step 201 and 202). When an alarm event is detected (step 201/yes), an alarm message is displayed on the screen of the display unit 117 (step 203) and user response is prompted. When the user acknowledges the alarm message by clicking the message, for example, the control and processing unit starts to search for control options for the user (steps 204 and 205). Here, the control and processing unit goes through different scenarios of the control model to find the control options that are available in the current alarm situation. In the embodiment of FIG. 2, each control option found does not only include the parameters/variables to be adjusted but also the preferred values to which these parameters/variables are to be adjusted by the user.

Upon finding the available control options, the control and processing unit may display the control options in priority order on the screen of the display unit (206). This screen view is in this context termed a control option view. From the control option view, the user may select a preferred control option (step 207/yes). In response to the selection of the control option, the control and processing unit opens a new control view termed adjustment view in this context (step 208). In the adjustment view, the user may acknowledge predefined settings of the selected control option or further adjust the settings from the predefined values determined by the control and processing unit, as shown in step 209. When the user has acknowledged the predefined settings or confirmed the adjusted values in step 209, the control and processing unit adjusts the settings of one or more care devices to correspond to the new values, cf. step 210 in FIG. 2 and arrow 119 in FIG. 1.

In some cases the control and processing unit may detect in step 205 that no control options exist that are sufficient in the current situation. For example, due to severe blood loss the concentration of carbon dioxide at the end of exhaled period (EtCO2) may rise too fast to be compensated by adjustment of the ventilator settings. In these cases the control and processing unit may escalate the alarm to quickly inform the user of the criticality of the situation.

Figure 3:
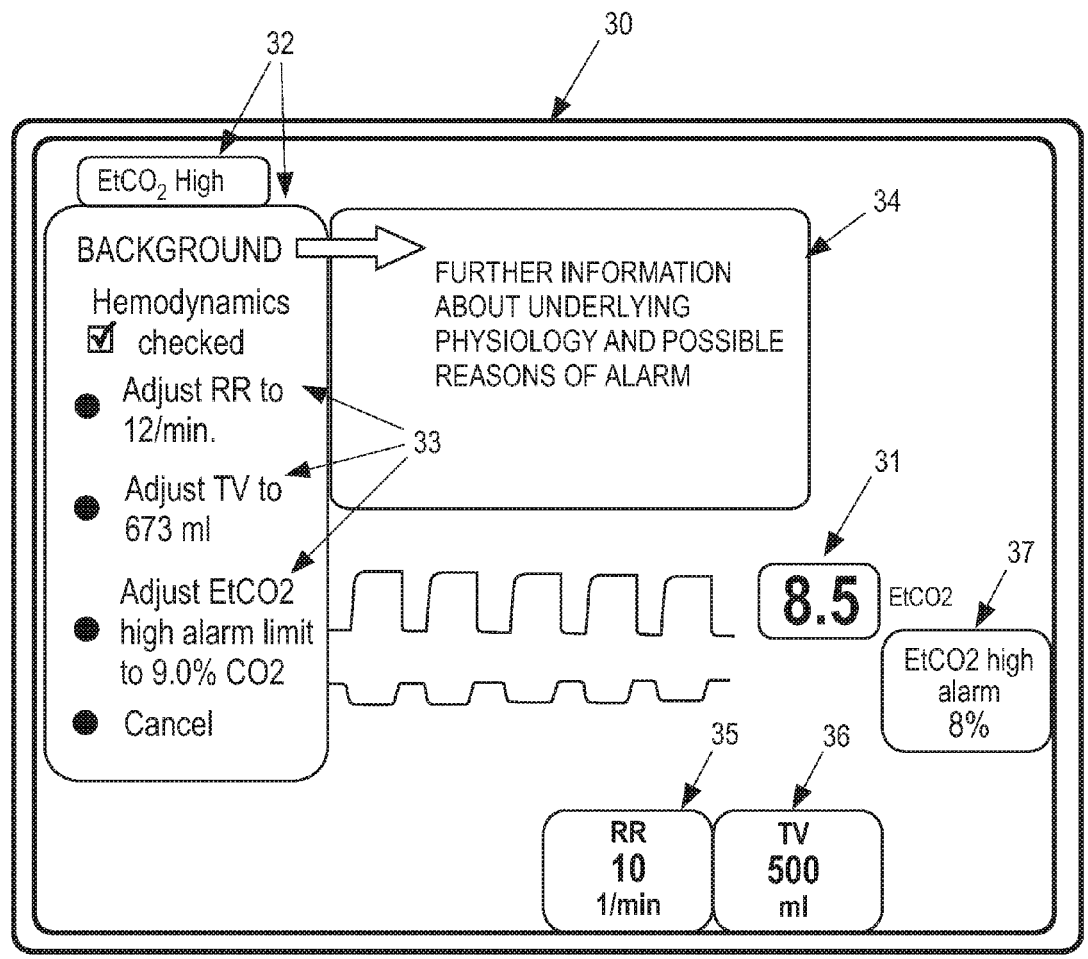
FIG. 3 illustrates one embodiment of a display view presented to the user in response to alarm acknowledgment.

FIG. 3 illustrates an example of the control option view 30. It is assumed here that new windows are opened on top of normal monitoring view. However, only the GUI components that relate to the alarm handling are presented in the figures. It is further assumed in this example that an alarm is raised since EtCO2 exceeds the respective (high) alarm limit value of 8%. In response to this, the reading indicating the current EtCO2 value, which is 8.5 in this example, is highlighted to form an alarm icon 31 that may also start to blink. Other visual and audible effects may also be used to alert the staff. When the user acknowledges the alarm by clicking the blinking alarm icon, for example, the control and processing unit starts to search for the available control options through the control model 111. When the available control options have been found, the control and processing unit may open a new window 32 that lists the available control options 33 in priority order in terms of this alarm event. In the example of the figure, the alarm event is indicated by a visual marker at the top of the window and the options are indicated by bullet characters within the window 32. In this example, the user also needs to confirm that the hemodynamics of the subject has been checked (respective check-box ticked in the figure). Window 32 may be linked to a further information window 34 that displays information about underlying physiology and possible alarm reasons to support the user in the selection of an appropriate control option. In this example, the information window 34 may thus include information about possible reasons for increased expired carbon dioxide and about the factors that need to be checked by the user to narrow down the number of possible alternatives causing the alarm. For example, the information window may first instruct the user to check whether only expired carbon dioxide is increased or whether both expired and inspired carbon dioxide are increased. Depending on the answer, the user may then be instructed to proceed through different paths to get an idea of the possible reasons and thus also to get assistance in selecting the most appropriate control option from the control view.

In addition to windows 32 and 34, the control option view may further display control icons 35-37 that correspond to the control options and indicate the current value related to the control option. In this example, the first option indicated in window 32 is to adjust respiration rate (RR) to a value of 12/min., the second option is to adjust tidal volume (TV) to 673 ml, and the third option is to adjust EtCO2 high alarm to a value of 9%. Correspondingly, the first control icon 35 indicates the current value of the respiration rate, the second control icon 36 indicates the current value of tidal volume, and the third control icon 37 indicates the current value of the alarm limit. The preferred control options, i.e. the first option in the list and the corresponding control icon 35, may also start blinking or may be presented with a different color to indicate that this is the recommended path for the user to proceed. The user may now select the desired control alternative by clicking the desired option in the list of window 32 or the corresponding control icon 35-37 near the lower right corner of the window.

Figure 4:
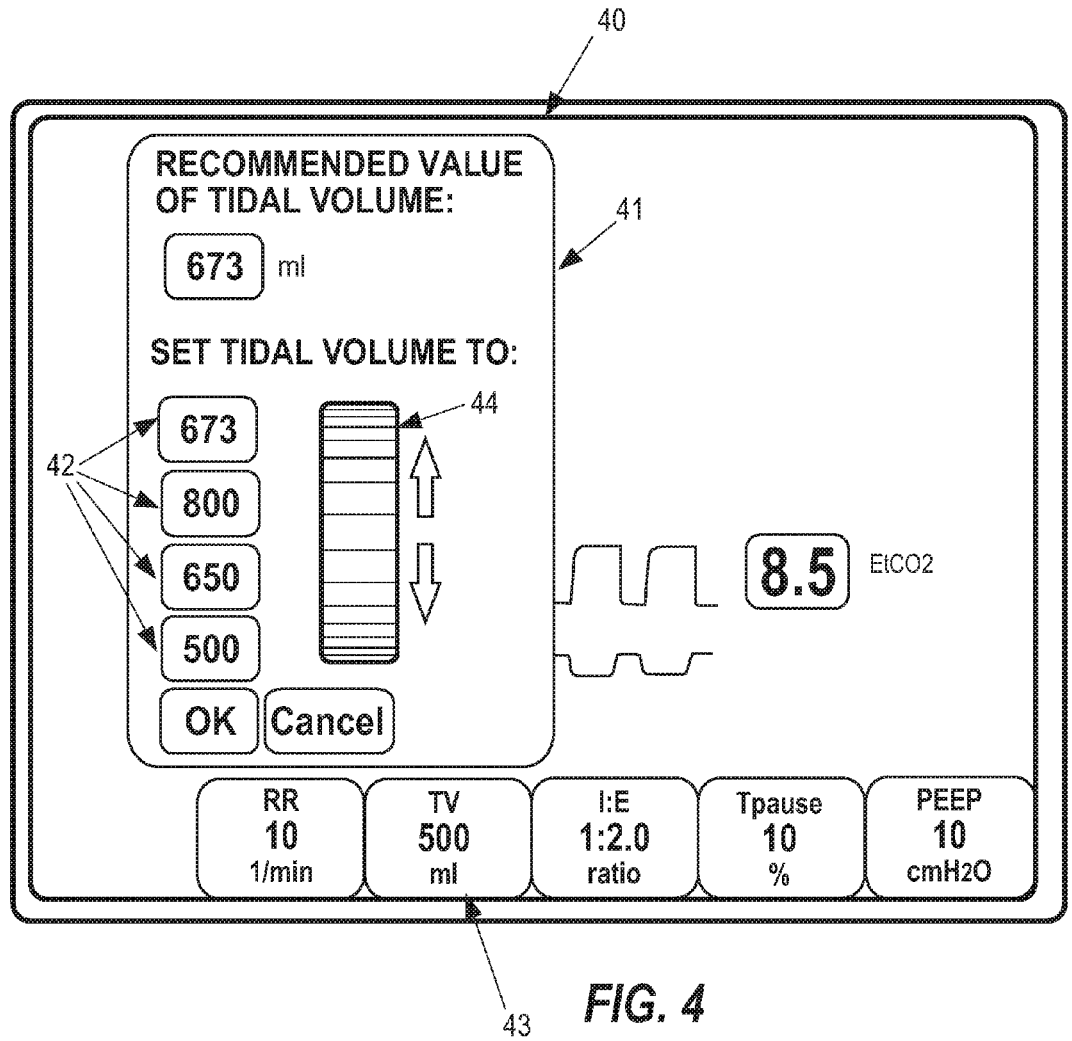
FIG. 4 illustrates one embodiment of a further display view presented to the user in response to a user-selected control option.

Upon selection of a control option, the display screen is updated to present the adjustment view to the user. FIG. 4 illustrates an example of the adjustment view 40. Now, the control and processing unit may open an adjustment window 41 indicating the current and recommended settings related to the selected control option. In this example, the user has selected the second control option from window 32, whereby the adjustment view indicates the current value of tidal volume and the recommended new value thereof. In this example, the current value is presented in a separate GUI element 43 at the bottom of the screen, while the opened adjustment window 41 indicates the recommended new value of tidal volume. Here, the adjustment window further includes buttons 42 that may be used to control the tidal volume to a particular value and a roller widget 44 through which the value of the parameter may be adjusted.

Figure 5:
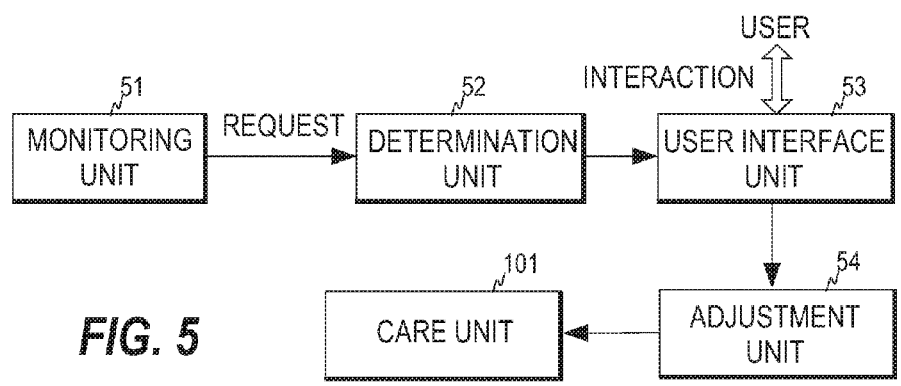
FIG. 5 illustrates an example of the functional entities of the control and processing unit of the apparatus/system in terms of alarm management.

In terms of the alarm management, the functionalities of the control and processing unit 106 may be divided into the units shown in FIG. 5. A monitoring unit 51 is configured to monitor physiological parameters obtained from the subject and to trigger an alarm in response to detection of a predetermined alarm event. A determination unit 52 is adapted to determine one or more available control options for recovering from the alarm event. The determination is carried out in response to a request from the monitoring unit, which is generated in response to an alarm event or in response a user acknowledgment of an alarm event. A user interface unit 53 is configured to interact with the user to obtain a user-selected control option with user-acknowledged settings and an adjustment unit 54 adapted to adjust the settings of the at least one care device according to the user-acknowledged settings. It is to be noted that FIG. 5 illustrates the division of the functionalities of the control and processing unit in logical sense and in view of the alarm management disclosed. In a real apparatus the functionalities may be distributed in different ways between the elements or units of the apparatus/system.

A conventional patient monitor may also be upgraded to enable alarm handling according to the above mechanism. Such an upgrade may be implemented, for example, by delivering to the monitor a plug-in unit that may include the software system, possibly with the control model if the model does not reside in the network. The plug-in unit may be delivered, for example, on a data carrier, such as a CD or a memory card, or the through a telecommunications network. Since a conventional patient monitor produces the time series of the physiological parameters, the plug-in unit may include only the software components that correspond to units 52-54 of FIG. 5. That is, the plug-in software unit may include a first portion adapted to determine at least one available control option for recovering from the alarm event, a second portion adapted to prompt a user to select one of the at least one available control option, thereby to obtain a user-selected control option, and a third portion adapted to adjust the settings of the at least one care device according to the user-selected control option, thereby to recover from an alarm event. The content of the first portion may vary depending on the location of the control model.

The above alarm management allows the subject to be returned to safe therapy immediately after problems occur, without worrying if the adjustment made is insufficient or excessive. Further, the time that the subject is in unsafe state may be reduced significantly.

The mechanism may be used in connection with various care processes, such as hypnosis (sleep), analgesia (pain), neuromuscular therapy (movement), oxygenation (inhaling), ventilation (exhaling), and perfusion (blood flow). Furthermore, the system may monitor for various types of alarm events and number of parameters to be adjusted may vary depending on the application. Depending on the care process, the control model may include various modules configured to predict the effect of the adjustment of the settings of the care device(s) on the physiological parameters relevant in the particular care process.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for managing alarms during a care process, the method comprising:
   providing care to a subject according to settings of at least one care device:
   monitoring physiological parameters obtained from the subject, wherein the monitoring comprises triggering an alarm in response to detection of an alarm event;
   employing a control model in a control unit adapted to model recovery strategies from the alarm event to normal state of the subject based on drug specific and patient specific parameters to determine a plurality of available control options for recovering from the alarm event;
   visually displaying the plurality of available control options in a priority order based on the effectiveness of each of the plurality of control options in a previous cases, wherein each of the available control options includes at least one preferred value for at least one of the settings of the at least one care device;
   prompting the user to select one of the plurality of control options, thereby to obtain a user-selected control option in the control unit; and
   operating the control unit to adjust the settings of the at least one care device according to the preferred value for the at least one of the settings included as part of the user-selected control option such that the at least one care device operates with the adjusted settings.

2. The method according to claim 1, wherein the prompting further comprises presenting decision-supportive information to the user.

3. The method according to claim 1, further comprising presenting to the user graphical user interface elements adapted to enable the user to adjust the settings from the at least one preferred value, wherein the presenting is performed in response to obtaining the user-selected control option and wherein the adjusting includes adjusting the settings to user-adjusted values when the user employs the graphical interface elements and to the at least one preferred value when the user omits to employ the graphical interface elements.

4. An arrangement for managing alarms during a care process, the arrangement comprising:
   at least one care device adapted to provide care to a subject according to settings of the care device;
   a monitoring unit in communication with the care device and adapted to monitor physiological parameters obtained from the subject, wherein the monitoring unit is further adapted to trigger an alarm in response to detection of an alarm event;
   a determination unit adapted to utilize a control model to model recovery strategies from the alarm event to a normal state of the subject based on drug specific and patient specific parameters to determine a plurality of available control options for recovering from the alarm event, wherein each of the plurality of control options includes at least one preferred value for at least one of the settings;
   a user interface unit configured to display the plurality of available control options in a priority order based on the effectiveness of each of the plurality of control options in previous cases and prompt a user to select one of the plurality of available control options, thereby to obtain a user-selected control option; and
   an adjustment unit in communication with the at least one care device and adapted to adjust settings of the at least one care device to the preferred value of the selected control option such that the at least one care device operates with the adjusted settings according to the user-selected control option.

5. The arrangement according to claim 4, wherein the determination unit is configured to employ a control model adapted to model recovery strategies from the alarm event to normal state of the subject.

6. The arrangement according to claim 4, wherein the user interface unit is further adapted to present decision-supportive information to the user.

7. The arrangement according to claim 4, wherein each of the at least one available control option includes at least one preferred value for the settings.

8. The arrangement according to claim 7, wherein the user interface unit is further adapted to present to the user graphical user interface elements adapted to enable the user to adjust the settings from the at least one preferred value.

9. A non-transitory computer-readable medium encoded with a computer program for managing alarms during a care process, the computer program product comprising:
- a first program product portion encoded on a computer-readable medium adapted to determine a plurality of available control options for recovering from an alarm event; and organize the plurality of available control options in a priority order based on the effectiveness of each of the plurality of control options in previous cases, wherein each of the control options includes a preferred value for at least one setting of a care device;
- a second program product portion encoded on a computer-readable medium adapted to prompt a user to select one of the plurality of available control options, thereby to obtain a user-selected control option; and
- a third program product portion encoded on a computer-readable medium adapted to adjust at least one setting of the at least one care device according, to the user-selected control option such that the at least one care device operates with the adjusted settings, 10. The computer program product according to claim 9, wherein the first program product portion comprises a control model adapted to model recovery strategies from the alarm event to normal monitoring state.

11. The method of claim 1 wherein the physiological parameters are monitored and the settings of the at least one care device are adjusted by the control unit separate from the at least one care device.

12. The method of claim 11 wherein the control unit is in communication with the at least one care device and adjusts the setting of the at least one care device based upon the user-selected control option.

* * * * *